US012736543B2

(12) United States Patent
Li et al.

(10) Patent No.: US 12,736,543 B2
(45) Date of Patent: Sep. 15, 2026

(54) ANTIGEN FOR 2019 NOVEL CORONAVIRUS AND DETECTION USE THEREOF

(71) Applicants: BEIJING WANTAI BIOLOGICAL PHARMACY ENTERPRISE CO., LTD., Beijing (CN); XIAMEN UNIVERSITY, Xiamen (CN)

(72) Inventors: Tingdong Li, Xiamen (CN); Qiaoyun Shi, Beijing (CN); Jinkai Ren, Beijing (CN); Shengxiang Ge, Xiamen (CN); Congming Hong, Xiamen (CN); Xiaolei Zhang, Beijing (CN); Dong Wang, Beijing (CN); Guoliang Zhou, Xiamen (CN); Quan Yuan, Xiamen (CN); Xiaowei Wu, Beijing (CN); Xuan Wang, Beijing (CN); Yangtao Wu, Xiamen (CN); Haifeng Pan, Xiamen (CN); Yuting Qi, Beijing (CN); Xuerong Jia, Beijing (CN); Lizhi Zhou, Xiamen (CN); Wangheng Hou, Xiamen (CN); Shan Qiao, Beijing (CN); Shaowei Li, Xiamen (CN); Jun Zhang, Xiamen (CN); Ningshao Xia, Xiamen (CN)

(73) Assignees: BEIJING WANTAI BIOLOGICAL PHARMACY ENTERPRISE CO., LTD., Beijing (CN); XIAMEN UNIVERSITY, Xiamen (CN)

( * ) Notice: Subject to any disclaimer, the term of this patent is extended or adjusted under 35 U.S.C. 154(b) by 1053 days.

(21) Appl. No.: 17/802,290

(22) PCT Filed: Jan. 18, 2021

(86) PCT No.: PCT/CN2021/072392
§ 371 (c)(1),
(2) Date: Aug. 25, 2022

(87) PCT Pub. No.: WO2021/169664
PCT Pub. Date: Sep. 2, 2021

(65) Prior Publication Data

US 2023/0358757 A1 Nov. 9, 2023

(30) Foreign Application Priority Data

Feb. 28, 2020 (CN) ........................ 202010131338.6

(51) Int. Cl.
*G01N 33/53* (2006.01)
*C07K 14/165* (2006.01)
*G01N 33/68* (2006.01)

(52) U.S. Cl.
CPC ....... *G01N 33/6854* (2013.01); *C07K 14/165* (2013.01); *C07K 2319/40* (2013.01); *G01N 2333/165* (2013.01); *G01N 2469/20* (2013.01)

(58) Field of Classification Search
CPC .. G01N 33/53; G01N 33/543; G01N 33/6854; G01N 2333/165; G01N 33/54353
See application file for complete search history.

(56) References Cited

U.S. PATENT DOCUMENTS

2010/0035231 A1 2/2010 Kumarsil et al.

FOREIGN PATENT DOCUMENTS

| | | | |
|---|---|---|---|
| CN | 1806175 | A | 7/2006 |
| CN | 104447986 | A | 3/2015 |
| CN | 111239392 | A | 6/2020 |
| EP | 3530668 | A1 | 8/2019 |
| WO | 2004109289 | A1 | 12/2004 |
| WO | 2007084692 | A2 | 7/2007 |
| WO | 2019175606 | A1 | 9/2019 |

OTHER PUBLICATIONS

Lederman et al. “A single amino acid substitution in a common African allele of the CD4 molecule ablates binding of the monoclonal antibody, OKT4” Mol Immunol. Nov. 1991;28(11): pp. 1171-1181. (Year: 1991).*

Colman et al. Research im Immunology, 1994; 145(1):pp. 33-36 (Year: 1994).*

Harlow, E. and Lan D., Antibodies: A Laboratory Manual (1988) Cold Spring Harbor Laboratory Press, Cold Spring Harbor, NY, pp. 23-26. (Year: 1988).*

He et al., A single amino acid substituation (R442A) in the receptor-binding domain of SARS coronavirus spike protein disrupts the antigenic structure and binding activity, Biochemical and Biphysical Research Communications 344, 2006, pp. 106-113. (Year: 2006).*

Chen et al., Double-antigen sandwich ELISA for detection of antibodies to SARS-associated coronavirus in human serum, Eur J Clin Microbiol Infect Dis (2005), 24: pp. 549-553. (Year: 2005).*

Wang et al., Detection of antibodies against SARS-CoV in serum from SARS-infected donors with ELISA and Western Blot, Clinical Immunology, 113, pp. 145-150 (Year: 2004).*

Fukushi, Shuetsu et al. “Characterization of novel monoclonal antibodies against the MERS-coronavirus spike protein and their application in species-independent antibody detection by competitive ELISA.” Journal of Virological Methods 251 (2017): 22-29.

Cao, Zhiliang et al. “Potent and persistent antibody responses against the receptor-binding domain of SARS-CoV spike protein in recovered patients.” Virology Journal 7 (2010): 299-299.

Supplementary European Search Report mailed on Feb. 28, 2024 in EP 21760161.6.

(Continued)

*Primary Examiner* — Gary Counts
(74) *Attorney, Agent, or Firm* — Honigman LLP

(57) ABSTRACT

Provided are a method for assaying a specific IgM antibody and a total antibody for the 2019 novel coronavirus (2019-nCOV), a method for determining whether subjects are infected with 2019-nCOV, and a virus antigen and a kit for carrying out the above-mentioned detection.

18 Claims, 1 Drawing Sheet

Specification includes a Sequence Listing.

(56) References Cited

OTHER PUBLICATIONS

PCT/CN2021/072392 International Search Report dated Apr. 15, 2021.

Chen, Fengping, et al, SARS: Changes of Serum Immunoglobulins and Complements Levels in Patients with SARS and an Analysis of the Results; Practical Preventive Medicine, vol. 12, No. 2, pp. 282-283; Apr. 30, 2005.

Lan, J., et al., Crystal structure of the 2019-nCoV spike receptor-binding domain bound with the ACE2 receptor; BioRxiv, Feb. 20, 2020, English portions only.

* cited by examiner

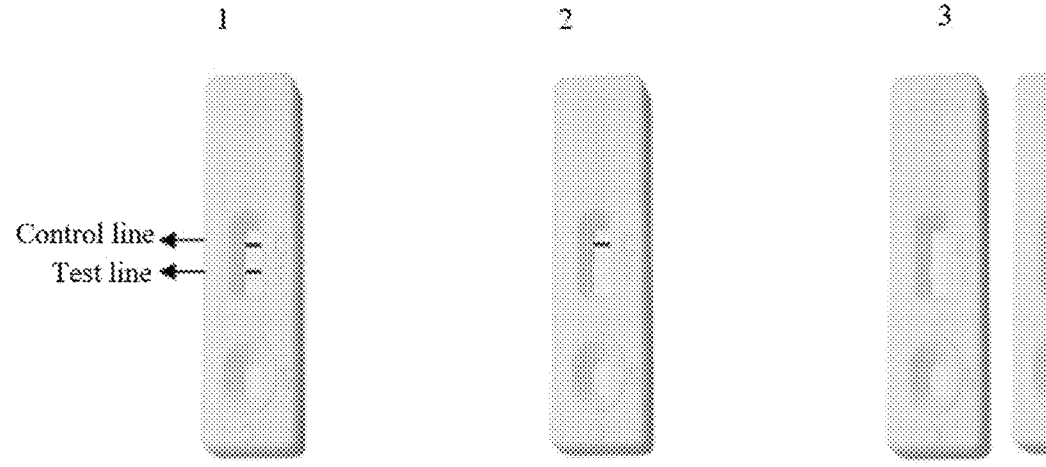
1
2
3
Control line
Test line

ANTIGEN FOR 2019 NOVEL CORONAVIRUS AND DETECTION USE THEREOF

CROSS-REFERENCE TO RELATED APPLICATIONS

This application is a National Stage Application and claims the benefit of priority under 35 U.S.C. § 371 to Patent Cooperation Treaty application PCT/CN2021/072392, filed Jan. 18, 2021, which claims the benefit of Chinese Patent Application No. 202010131338.6, filed Feb. 28, 2020. Priority is claimed to these applications and the disclosures of these prior applications are considered part of the disclosure of this application and to the extent allowed the entire contents of the aforementioned applications are incorporated herein.

SEQUENCE LISTING

This application incorporates by reference in its entirety the Sequence Listing entitled "2022-08-24_235427-515883_ST25.txt", is 2,379 bytes in size and was created on Aug. 24, 2022, and filed electronically herewith.

TECHNICAL FIELD

The present invention relates to the field of virological detection. Specifically, the present invention provides a method for detecting 2019-nCoV-specific IgM antibody and total antibody, a method for determining whether a subject is infected with 2019-nCoV, and a viral antigen and kit for the above detection.

BACKGROUND ART

"Severe acute respiratory syndrome coronavirus 2 (SARS-CoV-2)" is formerly known as "novel coronavirus" or "2019-nCov". SARS-CoV-2, novel coronavirus, and 2019-nCov have the same meaning and are used interchangeably herein. 2019-nCoV belongs to the genus Coronavirus, which are enveloped, single-stranded RNA viruses that can infect wild animals, pets, herds, and humans.

Coronaviruses belong to the family Coronaviridae and the order Nidoviridae, their particles are spherical or irregular in shape, enveloped, and with a size of 80 to 120 nm. The virus generally comprises spike protein (Spike, S), small envelope protein (Envelope, E), membrane protein (Membrane, M), and nucleocapsid protein (Nucleocapsid, N). According to the structural characteristics of their genomes, coronaviruses are currently divided into 4 genera, namely α, β, γ and δ. The 2019-nCoV virus is a new coronavirus belonging to the genus β, which is enveloped with round or oval particles, often pleomorphic, and having a diameter of 60 to 140 nm. S protein is the key protein of coronavirus for infecting cells, carries the main antigenic determinants of B lymphocyte, and is the only structural protein that can induce neutralizing antibodies to provide immune protection; it contains the recognition sites of host cell receptor, and plays a key role in determining host cell tropism; it also determines the pathogenicity of virus, and is the main determinant of the virulence of virus.

Current studies show that the 2019-nCoV virus can be transmitted through droplets, contact and fecal-oral transmission, and has an incubation period generally of 3 to 7 days, up to 21 days. The main clinical manifestations are fever, fatigue, and dry cough. A small number of patients have symptoms such as nasal congestion, runny nose, and diarrhea. Severe cases mostly develop dyspnea after one week, and more severe cases rapidly progress to acute respiratory distress syndrome, septic shock, metabolic acidosis that is difficult to correct, and coagulation dysfunction. It is worth noting that severe and critical patients may have moderate to low fever or even no obvious fever during the course of the disease. Some patients only showed low-grade fever, mild fatigue, etc., without pneumonia, and most of them recovered after 1 week. Although the 2019-nCoV virus is less lethal than avian influenza and the Middle East MERS virus, its transmission is very strong.

At present, the detection methods for 2019-nCoV virus are mainly nucleic acid detection methods such as fluorescent PCR method, but the nucleic acid detection is high in cost and complicated in operation, with an entire testing process of more than 2 hours, and there is a risk of infection and spread, hence it is necessary to perform the testing in a laboratory with biosafety level II or above, and thus it is difficult to meet the needs of large-scale screening. Therefore, it is urgent to develop a safe, efficient, and convenient method for detection of 2019-nCoV antibody. Immunological detection has high sensitivity and specificity, and the results are easy to analyze, which is very useful in influenza control, elimination and quarantine. At the same time, it has been reported that RT-PCR technology can be used to detect whether a patient is infected with the virus within the first 10 days of fever symptoms after SARS virus infection; however, false negative results are often found when RT-PCR is used in the later stage of the disease, while serological test results are more accurate at this stage. Therefore, a kit for the detection of 2019-nCoV virus antibodies can be developed to detect serum antibodies in large scale more conveniently and effectively.

Contents of the Present Invention

After extensive research, the inventors of the present application unexpectedly discovered a viral antigen that is particularly suitable for the detection of 2019-nCoV (SARS-CoV-2). Based on this, the present invention has successfully established a method for determining IgM antibody and total antibody specific to 2019-nCoV (SARS-CoV-2), and for determining whether a subject is infected with 2019-nCoV (SARS-CoV-2), having good repeatability, strong specificity and high sensitivity.

Viral Antigen Polypeptide

In a first aspect, the present invention provides an isolated polypeptide, which comprises or consists of an amino acid sequence selected from the group consisting of:

(i) the sequence shown in SEQ ID NO: 1;

(ii) a sequence having a substitution, deletion or addition of one or several amino acids (e.g., substitution, deletion or addition of 1, 2, 3, 4 or 5 amino acids) compared to the sequence shown in SEQ ID NO: 1; and (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% compared to the sequence shown in SEQ ID NO. 1.

The present invention also provides a fusion protein, which comprises the isolated polypeptide of the present invention and an additional polypeptide.

In certain embodiments, the additional polypeptide is attached to the N-terminus or C-terminus of the polypeptide of the present invention, optionally via a linker.

In certain embodiments, the additional polypeptide is selected from protein tags. In certain embodiments, the protein tag is well known in the art, examples of which include, but are not limited to, His, Flag, GST, MBP, HA, Myc, GFP, or Fc, etc., and those skilled in the art know how to select an appropriate protein tag for the intended purpose (e.g., purification, detection, tracking, solubilization, or protease protection, etc.).

The polypeptide or fusion protein of the present invention is not limited by its production method, for example, it can be produced by a genetic engineering method (recombinant technology) or chemical synthesis method.

Accordingly, the present invention also provides an isolated nucleic acid molecule, which comprises a nucleotide sequence encoding the isolated polypeptide or fusion protein as described above.

The present invention also provides a vector, which comprises the isolated nucleic acid molecule as described above. The vector of the present invention may be a cloning vector or an expression vector. In a preferred embodiment, the vector of the present invention is, for example, a plasmid, cosmid, phage, and the like.

The present invention also provides a host cell, which comprises the isolated nucleic acid molecule or vector as described above. Such host cell includes, but is not limited to, prokaryotic cell such as *E. coli* cell, and eukaryotic cell such as yeast cell, insect cell, plant cell, and animal cell (e.g., mammalian cell such as mouse cell, human cell, etc.). The cell of the present invention may also be a cell line, such as 293T cell.

The present invention also provides a method of preparing the isolated polypeptide or fusion protein as described above, which comprises, culturing the host cell as described above under conditions that allow the expression of the isolated polypeptide or fusion protein, and recovering the polypeptide or fusion protein from a culture of the cultured host cell.

In particular, the polypeptide or fusion protein of the present invention can be linked to an additional functional moiety.

In one embodiment, the isolated polypeptide or fusion protein of the present invention bears a detectable label.

As used herein, a "detectable label" may be any substance detectable by fluorescent, spectroscopic, photochemical, biochemical, immunological, electrical, optical or chemical means. It is particularly preferred that such label is suitable for immunological detection (e.g., enzyme-linked immunoassay, radioimmunoassay, fluorescence immunoassay, chemiluminescence immunoassay, immunocolloidal gold technique, etc.). Such label is well known in the art and includes, but is not limited to, enzyme (e.g., horseradish peroxidase, alkaline phosphatase, β-galactosidase, urease, glucose oxidase, etc.), radionuclide (e.g., $^{3}$H, $^{125}$I, $^{35}$S, $^{14}$C, or $^{32}$P) fluorescent dye (e.g., fluorescein isothiocyanate (FITC), fluorescein, tetramethylrhodamine isothiocyanate (TRITC), phycoerythrin (PE), Texas Red, rhodamine, quantum dot or cyanine derivative (e.g., Cy7, Alexa 750), luminescent substance (e.g., chemiluminescent substance, such as acridine ester compound), magnetic bead (e.g., Dynabeads®), calorimetric label such as colloidal gold or colored glass or plastic (e.g., polystyrene, polypropylene, latex, etc.) bead, and biotin for binding avidin (e.g., streptavidin) modified with the aforementioned label. The labels encompassed by the present invention can be detected by methods known in the art. For example, a radiolabel can be detected using photographic film or a scintillation calculator, and a fluorescent label can be detected using a light detector to detect the emitted light. An enzyme label is generally detected by providing a substrate to the enzyme and detecting the reaction product produced by the action of the enzyme on the substrate, and a calorimetric label is detected by simply visualizing the colored label. In certain embodiments, a detectable label as described above can be linked to the isolated polypeptide or fusion protein via a linker of variable length to reduce potential steric hindrance.

In certain embodiments, the detectable label is selected from enzyme (e.g., horseradish peroxidase or alkaline phosphatase), chemiluminescence reagent (e.g., acridine ester compound), fluorescent dye, colloidal gold, or biotin. In certain embodiments, the detectable label is selected from enzyme (e.g., horseradish peroxidase or alkaline phosphatase) or colloidal gold.

In another embodiment, the isolated polypeptide or fusion protein is attached to a surface of a solid support, or is able to be used to attach to a solid support.

As used herein, the solid support includes concave well plate, test tube, bead (e.g., latex particle) or membrane (e.g., nitrocellulose membrane) made of or coated with a polymeric material (e.g., polyvinyl chloride, polystyrene, polyacrylamide or cellulose), or magnetic bead pre-coated with a functional group (e.g., amino, carboxyl, biotin or avidin). In certain embodiments, the solid support is selected from magnetic bead, microtiter plate (e.g., microplate or ELISA plate), or nitrocellulose membrane.

Methods for coating proteins or polypeptides on solid supports are well known in the art, including, for example, physical adsorption, covalent coupling via aminated or carboxylated surface, or binding mediated by avidin-biotin system, polylysine-precoated surface, protein A- or protein G-precoated surface.

Therefore, in order to realize the attachment between the isolated polypeptide or fusion protein of the present invention and the solid support, the isolated polypeptide or fusion protein of the present invention may have a modifying group that can be linked to the solid support. In this case, the surface of the solid support bears a linking group corresponding to the modifying group. In certain embodiments, the modifying group is biotin or avidin, and accordingly, the surface of the solid support carries avidin for binding biotin or biotin for binding avidin.

Alternatively, the isolated polypeptide or fusion protein of the present invention may not bear the modifying group, but can be directly coated on the surface of the solid support in the presence of a coating buffer (e.g., carbonate buffer, phosphate buffer, Tris-HCL buffer or borate buffer).

Another object of the present invention is to provide uses of the isolated polypeptides of the present invention.

Detection of 2019-nCoV IgM Antibody

In one aspect, the isolated polypeptides or fusion proteins of the present invention can be used to detect IgM antibody specific to the novel coronavirus (2019-nCoV) in a sample from a subject.

IgM is the earliest antibody that appears in the body after antigen stimulation, so it usually can be used as an early diagnostic indicator of infectious diseases, and it is also strong evidence to distinguish recent infections from past infections. Since specific IgM against a certain antigen in serum often coexists with specific IgG, the specific IgM antibody is usually detected by a capture assay to avoid the interference of IgG on the detection of IgM, in which all serum IgM are first captured to remove IgG, followed by detecting the specific IgM.

Therefore, the isolated polypeptide or fusion protein described in the first aspect of the present invention can be used as a detection reagent to specifically detect the captured IgM antibody, so that the detection of 2019-nCoV IgM antibody can be realized by the capture assay. Detection of specific IgM antibody levels in a sample by capture assays is well known to those skilled in the art. In such detection, "capture reagent" first forms an immune complex with IgM antibody in a sample, and the captured antibody is then detected by the "detection antigen".

Therefore, in a second aspect, the present invention provides a kit, which comprises a detection reagent, the detection reagent is selected from the polypeptide or fusion protein of the present invention bearing a detectable label.

In certain embodiments, the kit further comprises a capture reagent, the capture reagent is selected from reagents capable of specifically binding to IgM.

In certain embodiments, the reagent capable of specifically binding to IgM is selected from anti-IgM (μ chain) antibodies or antigen-binding fragments thereof. In certain embodiments, the anti-IgM antibody or antigen-binding fragment thereof can be a monoclonal antibody. In certain embodiments, the anti-IgM antibody or antigen-binding fragment thereof can be a polyclonal antibody. In certain exemplary embodiments, the anti-IgM antibody or antigen-binding fragment thereof can be a murine anti-human IgM monoclonal or polyclonal antibody, a goat anti-human IgM monoclonal or polyclonal antibody, a rabbit anti-human IgM monoclonal or polyclonal antibody, etc.

In certain embodiments, the reagent capable of specifically binding to IgM is attached to a surface of a solid support, or is able to be used to attach to a solid support.

In order to realize the attachment between the reagent capable of specifically binding to IgM and the solid support, the reagent capable of specifically binding to IgM may have a modifying group that can be linked to the solid support. In this case, the surface of the solid support bears a linking group corresponding to the modifying group. In certain embodiments, the modifying group is biotin or avidin, and accordingly, the surface of the solid support carries avidin for binding biotin or biotin for binding avidin.

Alternatively, the reagent capable of specifically binding to IgM may not bear the modifying group, and can be directly coated on the surface of the solid support in the presence of a coating buffer (e.g., carbonate buffer, phosphate buffer, Tris-HCL buffer or borate buffer).

Thus, in certain embodiments, the kit may further comprise a coating reagent, such as a coating buffer (e.g., carbonate buffer, phosphate buffer, Tris-HCL buffer, or borate buffer), for coating the reagent capable of specifically binding to IgM on the solid support.

In certain embodiments, the kit further comprises a solid support. In certain embodiments, the solid support is selected from magnetic bead, microtiter plate (e.g., microplate or ELISA plate), or nitrocellulose membrane.

In certain embodiments, the kit further comprises an instruction of using the capture reagent and detection reagent to detect an IgM antibody specific to the novel coronavirus (2019-nCoV) in a sample from a subject, and optionally determine whether the subject has an infection with the novel coronavirus (2019-nCoV).

In certain embodiments, the kit further comprises one or more reagents or devices selected from: (i) a device for collecting or storing a sample from the subject (e.g., blood collection device); (ii) an additional reagent required for the detection (e.g., buffer, diluent, blocking solution, positive control sample, negative control sample, reagent for detecting detectable label); (iii) a coating solution for attaching the reagent capable of specifically binding to IgM to the surface of the solid support.

In certain exemplary embodiments, the detection is an enzyme-linked immunosorbent assay, and the additional reagent required for the detection comprise one or more selected from the group consisting of: a positive control sample, a negative control sample (e.g., buffer solution containing BSA), a concentrated washing solution containing not less than 2.5% surfactant, Developer A containing not less than 0.3 g/L of peroxide, Developer B containing not less than 0.2 g/L of TMB, and a termination solution containing not more than 2 mol/L of sulfuric acid.

In a third aspect, the present invention provides a method for detecting an IgM antibody specific to the novel coronavirus (2019-nCoV) in a sample from a subject, which is based on a capture assay, comprising:

(1) contacting the sample with a capture reagent to obtain an immune complex; the capture reagent is selected from a reagent capable of specifically binding to IgM;

(2) detecting the immune complex (the presence or amount of the complex) obtained in step (1) by immunological detection using a detection reagent; the detection reagent is selected from the isolated polypeptide or fusion protein described in the first aspect.

As used herein, the term "immunological detection" refers to a detection that is performed by utilizing a specific interaction/binding affinity between antigen-antibody, which can generally be used to detect the presence or level of a particular antigen or antibody in a sample. Such immunological detection is well known to those skilled in the art, and includes, but is not limited to, enzyme immunoassay (EIA), chemiluminescence immunoassay (CLIA), radioimmunoassay (RIA), fluorescence immunoassay (FIA), Western blotting, immunoturbidimetry, surface plasmon resonance, immunocolloidal gold (ICG), immunochromatography, etc.

In certain embodiments, the immunological detection is selected from enzyme immunoassay (e.g., ELISA), chemiluminescence immunoassay, fluorescence immunoassay, radioimmunoassay, or immunocolloidal gold technique (ICG).

In certain embodiments, the method is used to detect the presence of IgM antibody specific to 2019-nCoV in the sample.

In certain embodiments, in step (2), the detection reagent can bear a detectable label, and the immunological detection is achieved by measuring the detectable label.

In certain embodiments, the method further comprises: (3) comparing the detection value obtained in step (2) with a predetermined cut-off value. In certain embodiments, if the detection value is not lower than the cut-off value, the sample is determined to be positive for 2019-nCoV-specific IgM antibody.

In certain embodiments, the sample is a blood sample, such as whole blood, plasma, or serum.

In certain embodiments, the subject is a human. In certain embodiments, the subject is at risk for a novel coronavirus (2019-nCoV) infection.

In certain embodiments, the capture reagent is attached to the surface of a solid support.

In certain embodiments, prior to step (1), the method optionally further comprises a step of coating the capture reagent on the surface of the solid support. In such embodiments, the capture reagent may bear a modifying group that can be attached to the solid support, or may not bear a modifying group but can be directly coated on the surface of the solid support.

In a fourth aspect, the present invention provides a method for determining whether a subject has a novel coronavirus (2019-nCoV) infection, which comprises:

(i) detecting the level of IgM antibody specific to novel coronavirus (2019-nCoV) in a sample from a subject by the method described in the third aspect; and, (ii) comparing the level with a reference value to determine whether the subject has a novel coronavirus (2019-nCoV) infection.

In certain embodiments, the reference value may include a negative reference value, and the negative reference value is a corresponding level value derived from a subject who is not infected with 2019-nCoV or a healthy person (e.g., a subject without detectable disease, and/or without a history of viral infection or 2019-nCoV infection), or a value obtained by detecting a sample derived from a subject without 2019-nCoV infection or a healthy person by the method described above. When compared with the negative reference value, if the level obtained in step (i) is higher than the reference value, it is determined that the subject has a novel coronavirus (2019-nCoV) infection.

In certain embodiments, the reference value may comprise a positive reference value, and the positive reference refers to a corresponding level value derived from a subject or patient known to have 2019-nCoV infection, or a value obtained by detecting a sample from a subject or patient known to be infected with 2019-nCoV. When compared with the positive reference value, if the level obtained in step (i) is not lower than the reference value, it is determined that the subject has a novel coronavirus (2019-nCoV) infection.

In certain embodiments, the method comprises:

(i) detecting the presence of IgM antibody specific to novel coronavirus (2019-nCoV) in a sample from a subject by the method described in the third aspect; and, (ii) when the presence of IgM antibody is detected, it is determined that the subject has a novel coronavirus (2019-nCoV) infection.

In certain embodiments, when the sample from the subject is determined to be positive for 2019-nCoV-specific IgM antibody based on the comparison of the detected value (e.g., absorbance) of the sample with a predetermined cutoff value, the subject is determined to have a novel coronavirus (2019-nCoV) infection (e.g., recent infection).

In certain embodiments, the sample is a blood sample, such as whole blood, plasma, or serum.

In certain embodiments, the subject is a human. In certain embodiments, the subject is at risk for a novel coronavirus (2019-nCoV) infection.

In certain embodiments, the method further comprises:

prior to step (i), providing a sample from the subject; and/or after step (ii), administering to the subject determined to be infected with the novel coronavirus (2019-nCoV) a therapeutically effective amount of an antiviral therapy (e.g., an antiviral drug, such as lopinavir, ritonavir, interferon α, arbidol, ribavirin, prezista, cobicistat, remdesivir, baloxavir marboxil, favipiravir, chloroquine, hydroxychloroquine, etc.) that can treat the novel coronavirus (2019-nCoV) infection.

In a fifth aspect, the present invention provides use of the isolated polypeptide or fusion protein described in the first aspect in the manufacture of a kit for detecting an IgM antibody specific to novel coronavirus (2019-nCoV) in a sample from a subject or determining whether a subject has a novel coronavirus (2019-nCoV) infection.

In certain embodiments, the isolated polypeptide or fusion protein bears a detectable label.

In certain embodiments, the sample is a blood sample, such as whole blood, plasma, or serum.

In certain embodiments, the subject is a human. In certain embodiments, the subject is at risk of a novel coronavirus (2019-nCoV) infection.

In certain embodiments, the kit further comprises a reagent capable of specifically binding to IgM, such as an anti-IgM antibody or antigen-binding fragment thereof.

In certain embodiments, the reagent capable of specifically binding to IgM is attached to the surface of a solid support, or has a modifying group (e.g., biotin or avidin) that can be attached to the solid support.

In certain embodiments, the kit is used to detect the IgM antibody specific to the novel coronavirus (2019-nCoV) in the sample from the subject by the method described in the third aspect.

In certain embodiments, the kit is used to determine whether the subject has the novel coronavirus (2019-nCoV) infection by the method described in the fourth aspect.

Detection of 2019-nCoV Total Antibody

In another aspect, the isolated polypeptide of the present invention can be used to detect total antibody specific to the novel coronavirus (2019-nCoV) in a sample from a subject. The total antibody refer to all antibodies specific to 2019-nCoV in the sample, and are not limited to any classes, thus including IgM, IgG, IgA, etc.

Therefore, the isolated polypeptide or fusion protein described in the first aspect of the present invention can be used as a capture reagent to capture anti-2019-nCoV antibodies in the sample, and also can be used as a detection reagent to detect the captured anti-2019-nCoV antibodies, to achieve the detection of total antibody specific to 2019-nCoV by a double antigen sandwich method. Detection of specific antibody levels in a sample by double antigen sandwich methods is well known to those skilled in the art. In such detection, "capture antigen" and "detection antigen" allow the antibody in sample to form a bridge between the two specific antigens, therefore the two antigens are usually the same, or have the same core epitope, or have immunological cross-reactivity, which allows one antibody to bind the two antigens.

In a sixth aspect, the present invention provides a kit, which comprises a detection reagent, which is selected from the polypeptide or fusion protein of the present invention bearing a detectable label.

In certain embodiments, the kit further comprises a capture reagent, which is selected from the isolated polypeptide or fusion protein of the first aspect.

In certain embodiments, the polypeptide sequences (e.g., the antigenic polypeptide described in the first aspect) contained in the detection reagent and the capture reagent are identical or substantially identical. The term "substantially identical" means that the two polypeptide sequences contained in the detection reagent and the capture reagent differ from each other only by a substitution, deletion or addition of one or several amino acids (e.g., a substitution, deletion or addition of 1, 2, 3, 4 or 5 amino acid), or have a sequence identity of at least 80%, at least 85%, at least 90%, at least 91%, at least 92%, at least 93%, at least 94%, at least 95%, at least 96%, at least 97%, at least 98%, at least 99%, or 100%, and both polypeptide sequences are capable of being recognized and bound by anti-2019-nCoV antibodies.

In certain embodiments, the capture reagent is attached to the surface of a solid support, or is able to be used to attach to a solid support.

In order to realize the attachment of the capture reagent to the solid support, the capture reagent may have a modifying group that can be attached to the solid support. In this case, the surface of the solid support bears a linking group corresponding to the modifying group. In certain embodiments, the modifying group is biotin or avidin, and accordingly, the surface of the solid support carries avidin for binding biotin or biotin for binding avidin.

Alternatively, the capture reagent may not bear the modifying group, but can be directly coated on the surface of the solid support in the presence of a coating buffer (e.g., carbonate buffer, phosphate buffer, Tris-HCL buffer, or borate buffer).

Thus, in certain embodiments, the kit may further comprise a coating reagent for coating the capture reagent on the solid support, for example, a coating buffer (e.g., carbonate buffer, phosphate buffer, Tris-HCL buffer, or borate buffer).

In certain embodiments, the kit further comprises a solid support. In certain embodiments, the solid support is selected from magnetic bead, microtiter plate (e.g., microplate or ELISA plate), or nitrocellulose membrane.

In certain embodiments, the kit further comprises an instruction of using the capture reagent and the detection reagent to detect antibodies (i.e., total antibody) specific to the novel coronavirus (2019-nCoV) in a sample from a subject, and optionally, to determine whether the subject has a novel coronavirus (2019-nCoV) infection.

In certain embodiments, the kit further comprises one or more reagents or devices selected from the group consisting of: (i) a device for collecting or storing a sample from a subject (e.g., a blood collection device); (ii) an additional reagent required to perform the detection (e.g., buffer, diluent, blocking solution, positive control sample, negative control sample, reagent for detecting detectable label); (iii) a coating solution used to link the capture reagent to the surface of the solid support.

In certain exemplary embodiments, the detection is an enzyme-linked immunosorbent assay, and the additional reagent required for performing the detection comprise one or more selected from the group consisting of: a positive control sample, a negative control sample (e.g., buffer solution containing BSA), a concentrated washing solution containing not less than 2.5% of surfactant, Developer A containing not less than 0.3 g/L of peroxide, Developer r B containing not less than 0.2 g/L of TMB, and a termination solution containing not more than 2 mol/L of sulfuric acid.

In a seventh aspect, the present invention provides a method for detecting antibodies (i.e., total antibody) specific to novel coronavirus (2019-nCoV) in a sample from a subject, which is based on a double antigen sandwich method, comprising:

(1) contacting the sample with a capture reagent to obtain an immune complex; the capture reagent is selected from the isolated polypeptide or fusion protein described in the first aspect;

(2) detecting the immune complex (the presence or amount of the complex) obtained in step (1) by immunological detection using a detection reagent; the detection reagent is selected from the isolated polypeptide or fusion protein described in the first aspect.

In certain embodiments, the method is used to detect the presence of antibodies specific to 2019-nCoV in the sample.

In certain embodiments, in step (2), the detection reagent bears a detectable label, and the immunological detection is achieved by detecting the detectable label.

In certain embodiments, the immunological detection is selected from enzyme immunoassay (e.g., ELISA), chemiluminescence immunoassay, fluorescence immunoassay, radioimmunoassay, or immunocolloidal gold technique (ICG).

In certain embodiments, the method further comprises: (3) comparing the detection value obtained in step (2) with a predetermined cut-off value. In certain embodiments, if the detection value is not lower than the cut-off value, the sample is determined to be positive for 2019-nCoV-specific antibodies.

In certain embodiments, the sample is a blood sample, such as whole blood, plasma, or serum.

In certain embodiments, the subject is a human. In certain embodiments, the subject is at risk for a novel coronavirus (2019-nCoV) infection.

In certain embodiments, the capture reagent is attached to the surface of a solid support.

In certain embodiments, prior to step (1), the method optionally further comprises a step of coating the capture reagent on the surface of the solid support. In such embodiments, the capture reagent may bear a modifying group that can be attached to the solid support, or may not bear a modifying group but can be directly coated on the surface of the solid support.

In an eighth aspect, the present invention provides a method for determining whether a subject has a novel coronavirus (2019-nCoV) infection, comprising:

(i) detecting the level of antibodies (i.e., total antibody) specific to novel coronavirus (2019-nCoV) in a sample from the subject by the method described in the seventh aspect; and, (ii) comparing the level with a reference value to determine whether the subject has a novel coronavirus (2019-nCoV) infection.

In certain embodiments, the reference value may comprise a negative reference value, the negative reference value is derived from a subject who is not infected with 2019-nCoV or a healthy person (e.g., a subject without detectable disease, and/or without a history of viral infection or 2019-nCoV infection), or a value obtained by detecting a sample derived from a subject not infected with 2019-nCoV or a healthy person by the method described above. When compared with the negative reference value, if the level obtained in step (i) is higher than the reference value, it is determined that the subject has a novel coronavirus (2019-nCoV) infection.

In certain embodiments, the reference value may comprise a positive reference value, the positive reference value refers to a corresponding level value derived from a subject or patient known to have 2019-nCoV infection, or a value obtained after detecting a sample from a subject or patient known to be infected with 2019-nCoV by the method described above. When compared with the positive reference value, if the level obtained in step (i) is not lower than the reference value, it is determined that the subject has a novel coronavirus (2019-nCoV) infection.

In certain embodiments, the method comprises:

(i) detecting the presence of antibodies specific to the novel coronavirus (2019-nCoV) in a sample from the subject by the method described in the seventh aspect; and, (ii) when the presence of the antibody is detected, it is determined that the subject has a novel coronavirus (2019-nCoV) infection.

In certain embodiments, the subject is determined to a novel coronavirus (2019-nCoV) infection when a sample from the subject is determined to be positive for 2019-nCoV-specific antibodies based on the comparison of the detected value (e.g., absorbance) of the sample with a predetermined cut-off value.

In certain embodiments, the sample is a blood sample, such as whole blood, plasma, or serum.

In certain embodiments, the subject is a human. In certain embodiments, the subject is at risk for a novel coronavirus (2019-nCoV) infection.

In certain embodiments, the method further comprises:

prior to step (i), providing a sample from the subject; and/or after step (ii), administering to the subject determined to be infected with the novel coronavirus (2019-nCoV) a therapeutically effective amount of an antiviral therapy (e.g., an antiviral drug, such as lopinavir, ritonavir, interferon α, arbidol, ribavirin, prezista, cobicistat, remdesivir, baloxavir marboxil, favipiravir, chloroquine, hydroxychloroquine, etc.) that can treat the novel coronavirus (2019-nCoV) infection.

In a ninth aspect, the present invention provides use of the isolated polypeptide or fusion protein of the first aspect in the manufacture of a kit for detecting antibodies (i.e., total antibody) specific to the novel coronavirus (2019-nCoV) in a sample from a subject, or for determining whether a subject has a novel coronavirus (2019-nCoV) infection.

In certain embodiments, the kit comprises a capture reagent and a detection reagent, wherein the capture reagent is selected from the isolated polypeptide or fusion protein of the first aspect, and the detection reagent is selected from the isolated polypeptide or fusion protein bearing a detectable label.

In certain embodiments, the capture reagent is attached to the surface of a solid support, or has a modifying group (e.g., biotin or avidin) that can be attached to the solid support.

In certain embodiments, the sample is a blood sample, such as whole blood, plasma, or serum.

In certain embodiments, the subject is a human. In certain embodiments, the subject is at risk for a novel coronavirus (2019-nCoV) infection.

In certain embodiments, the kit is used to detect antibodies (i.e., total antibody) specific to the novel coronavirus (2019-nCoV) in a sample from a subject by the method described in the seventh aspect.

In certain embodiments, the kit is used to determine whether the subject has a novel coronavirus (2019-nCoV) infection by the method described in the eighth aspect.

Beneficial Effects

The present invention discovers for the first time a viral antigen that is particularly suitable for the detection of 2019-nCoV. Based on this, the present invention has further successfully established a method and kid for detecting IgM antibody and total antibody specific to 2019-nCoV, as well as for determining whether a subject is infected with 2019-nCoV infection. Compared with other viral antigen sequences, the detection method and kit based on the viral antigen sequence of the present invention can significantly improve the efficiency of detection of 2019-nCoV antibodies, having good repeatability, strong specificity and high sensitivity, showing important clinical significance for 2019-nCoV infection screening, thereby have broad market prospects and good economic and social benefits.

The embodiments of the present invention will be described in detail below with reference to the drawings and examples, but those skilled in the art will understand that the following drawings and examples are only used to illustrate the present invention, rather than limit the scope of the present invention. Various objects and advantageous aspects of the present invention will become apparent to those skilled in the art from the accompanying drawings and the following detailed description of the preferred embodiments.

BRIEF DESCRIPTION OF THE DRAWINGS

FIG. 1 shows a schematic diagram of determination of the detection results obtained by the colloidal gold method.

SEQUENCE INFORMATION

| SEQ ID NO | Description | Sequence information |
|---|---|---|
| 1 | 2019-nCoV S-RBD | RVQPTESIVRFPNITNLCPFGEVFNATRFASVYAWNRK RISNCVADYSVLYNSASFSTFKCYGVSPTKLNDLCFTN VYADSFVIRGDEVRQIAPGQTGKIADYNYKLPDDFTG CVIAWNSNNLDSKVGGNYNYLYRLFRKSNLKPFERDI STEIYQAGSTPCNGVEGFNCYFPLQSYGFQPTNGVGY QPYRVVVLSFELLHAPATVCGPKKSTNLVKNKCVNF |

EXAMPLES

Example 1: Detection Kit and Method for Detecting 2019-nCoV IgM Antibody (Enzyme-Linked Immunosorbent Assay)

1.1 Preparation of Detection Kit

The detection kit comprised: a 96-well ELISA plate coated with anti-human IgM, a 2019-nCoV-Ag enzyme labeled reagent labeled with horseradish peroxidase, a PBS buffer, a positive control containing 2019-nCoV-IgM positive sample, a negative control, a concentrated washing solution containing not less than 2.5% of surfactant, Developer A containing not less than 0.3 g/L of peroxide, Developer B containing not less than 0.2 g/L of TMB, and a termination solution containing not more than 2 mol/L of sulfuric acid.

Negative control: BSA 0.5 g/L, NaCl 137 mmol/L, KCl 2.7 mmol/L, $Na_2HPO_4$ 4.3 mmol/L, $KH_2PO_4$ 1.4 mmol/L.

Concentrated washing solution: TWEEN® 20 (Polysorbate 20) 30 ml/L, NaCl 2 mol/L, KCl 54 mmol/L, $Na_2HPO_4$ 80 mmol/L, $KH_2PO_4$ 28 mmol/L.

Color developing solution A: sodium acetate 27.2 g/L, citric acid 3.2 g/L, 30% hydrogen peroxide 0.6 ml/L.

Color developing solution B: disodium EDTA 0.4 g/L, citric acid 2 g/L, glycerol 100 ml/L, 0.3 g/L TMB.

Termination solution: sulfuric acid 2 mol/L.

Preparation of 96-Well ELISA Plate with Anti-Human IgM:

1. Murine anti-human IgM (μ chain) (Beijing Wantai Bio-Pharmaceutical Co., Ltd.) was formulated into a coating solution with 1×PBS buffer, and placed at 100 ul/well in the support plate overnight at 2-8° C.
2. PBS buffer containing 0.1% BSA was used at 200/well to perform blocking at 2-8° C. overnight.
3. The blocking solution was discarded, and drying was performed in a dry environment. Then, it was packed in an aluminum foil bag with desiccant.

Preparation of 2019-nCoV-Ag Enzyme Labeled Reagent with Horseradish Peroxidase:

1. 2019-nCoV-Ag fusion protein containing SEQ ID NO: 1 and a protein tag was dialyzed into CB (pH9.6, 50 mM), in which the medium was changed more than 2 times.

2. The $ddH_2O$ solution of HRP and the $ddH_2O$ solution of $NaIO_4$ were prepared.
3. The $NaIO_4$ solution was slowly mixed with the HRP solution, and allowed to stand at 4° C. for 30 min.
4. Ethylene glycol was slowly added to the oxidized HRP solution, and allowed to stand for 30 minutes at room temperature in the dark.
5. The oxidized HRP was directly added to the fully dialyzed viral antigen protein.
6. Dialysis into CB (pH9.6, 50 mM) was continued, in which the medium was changed more than 2 times.
7. $NaBH_4$ was added to it and allowed to stand at 4° C. for 2 hours.
8. 1×PBS buffer was allowed to stand overnight, the labeling solution was added with an equal volume of 50% glycerol, mixed well and stored at −20° C.

1.2 Detection Method

1. Preparation of solution: Concentrated washing solution was diluted 20 times with distilled water or deionized water.
2. Numbering: Samples were numbered corresponding to microplates in sequence. For each plate, 3 wells of negative control, 2 wells of positive control and 1 well of blank control were set. (When dual-wavelength detection was used, blank control wells could be omitted).
3. Addition of diluent: 100 μl of sample diluent was added to each well, except for negative- and positive control wells and blank wells.
4. Addition of samples: 10 μl of serum or plasma sample, and 100 μl of each of negative and positive controls were added to the corresponding wells, respectively, and mixed with gentle shaking.
5. Incubation: After sealing the plate with sealing film, incubation was performed at 37° C. for 30 minutes.
6. Washing plate: The sealing film was carefully removed, and the plate was washed with a plate washer 5 times, and at the end of last washing, the plate was inverted and tapped to completely drain as much as possible.
7. Addition of enzyme: 100 μl of the enzyme labeled reagent was added to each well, except for the blank well.
8. Incubation: the operation was the same as step 5.
9. Washing plate: the operation was the same as step 6.
10. Color development: 50 μl of color Developer A solution and 50 μl of color Developer B solution were added to each well, gently shaken and mixed, and color development was performed at 37° C. for 15 minutes in the dark.
11. Detection: 50 μl of the termination solution was added to each well, gently shaken and mixed, and the detection results were obtained within 10 minutes. The wavelength of microplate reader was set at 450 nm (or detected with dual wavelengths of 450 nm/600-650 nm), and the A value of each well was measured after zeroing using the blank well.

Judgement of Detection Results:

1. Normal range of negative control: the A value of the negative control well was less than or equal to 0.1 (if the A value of the negative control in one well was greater than 0.1, it should be discarded; if the A values of the negative control in two or more wells were greater than 0.1, the experiment should be repeated).
2. Normal range of positive control: the A value of the positive control well was ≥0.8.
3. Calculation of cut-off value (CUTOFF): cut-off value=mean of A values of negative control wells (Nc)×2.1 (if the value of negative control well was lower than 0.05, it should be calculated as 0.05). Positive judgment: sample with A value≥cut-off value (CUTOFF) was positive for 2019-nCoV-IgM antibody; negative judgment: sample with A value<cut-off value (CUTOFF) was negative for 2019-nCoV-IgM antibody.

1.3 Evaluation of Detection Performance (1) The above detection kit was used as candidate reagent to detect 2019-nCoV IgM antibody in plasma samples from 49 confirmed cases and 2 negative cases of Hubei Province. Among the 49 confirmed cases, 1 plasma sample was collected from each of 44 cases, and 2 plasma samples were collected at different periods from each of the remaining 5 cases, so that a total of 54 plasma samples were collected from the confirmed cases in this experiment. The candidate reagent detected 47 positive cases, and the detection rate of the candidate reagent compared with the confirmed cases was 95.92% (47/49). For the 2 negative cases, there were 1 sample from one subject, and 2 samples from another subject at two different periods, that was, there were a total of 3 negative samples. The results of the candidate reagent for the three negative samples were all negative.

(2) The above detection kit was used as candidate reagent to detect 2019-nCoV IgM antibody in 312 serum samples from 81 confirmed cases of novel coronavirus pneumonia at different times after onset in Zhejiang Province, and 300 serum samples from 300 other cases.

The detection results of the candidate reagent and the clinically confirmed/excluded results were analyzed by contingency table (four-fold table) for Kappa consistency test. The results showed that the sensitivity of the candidate reagent was 91.36% (95% confidence interval was 83.00% to 96.45%), the specificity was 100.00% (95% confidence interval was 96.38% to 100.00%), the accuracy was 98.16% (95% confidence interval was 96.25% to 99.26%), the Kappa value was 0.94, and the consistency strength was the strongest.

(3) Analysis of detection results of samples of different times after onset:

The above detection kit was used as candidate reagent to detect 2019-nCoV IgM antibody in plasma samples from confirmed cases of novel coronavirus pneumonia at different times after onset in Guangdong Province, and the detection results were taken together with those of samples of different times after onset in (2). The results were shown in the table below.

TABLE 2

Detection results of samples of different times after onset

| Days after onset | Candidate reagent | | |
|---|---|---|---|
| | Total number of detected samples (samples) | Number of positive of detection (samples) | Positive rate of detection |
| 1 | 3 | 2 | 66.67% |
| 2 | 12 | 2 | 16.67% |
| 3 | 21 | 5 | 23.81% |
| 4 | 26 | 4 | 15.38% |
| 5 | 28 | 7 | 25.00% |
| 6 | 49 | 12 | 24.49% |
| 7 | 47 | 18 | 38.30% |
| 8 | 54 | 22 | 40.74% |
| 9 | 62 | 23 | 37.10% |
| 10 | 52 | 32 | 61.54% |
| 11 | 54 | 41 | 75.93% |
| 12 | 61 | 48 | 78.69% |

TABLE 2-continued

| Detection results of samples of different times after onset | | | |
|---|---|---|---|
| Days | Candidate reagent | | |
| after onset | Total number of detected samples (samples) | Number of positive of detection (samples) | Positive rate of detection |
| 13 | 42 | 35 | 83.33% |
| 14 | 41 | 34 | 82.93% |
| 15 | 40 | 33 | 82.50% |
| 16 | 33 | 30 | 90.91% |
| 17 | 42 | 34 | 80.95% |
| 18 | 31 | 26 | 83.87% |
| 19 | 33 | 31 | 93.94% |
| ≥20 | 95 | 90 | 94.74% |

It could be seen from the above table that the detection rate of the candidate reagent in the early stage of onset (before day 7) was 15% to 40%, reached up to 40% to 80% 7 days after onset and reached up to 80% to 95% 15 days after onset. According to different period after onset, there were 5 cases in the very early stage (≤3 days) and 13 cases in the early stage (4-7 days) that were detected to be negative in the nucleic acid detection, while the candidate reagent could detect 2 cases (40%) and 6 cases (46%) from them, respectively; there were 29 cases in the middle stage (8-14 days) and 23 cases in the late stage (≥15 days) that were detected to be negative in the nucleic acid detection, while the candidate reagent could detect 24 cases and 21 cases, respectively.

The above results show that the ELISA-based IgM antibody detection can be used for the screening of 2019-nCoV infection, and has a good complementary effect on the nucleic acid detection.

Example 2: Detection Kit and Method for Determining Total Antibody Against 2019-nCoV (Enzyme-Linked Immunosorbent Assay)

2.1 Preparation of Detection Kit

The detection kit comprised: a 96-well ELISA plate coated with 2019-nCoV-Ag fusion protein containing SEQ ID NO: 1 and protein tag, a 2019-nCoV-Ag enzyme labeled reagent with horseradish peroxidase, a PBS buffer, a positive control containing 2019-nCoV antibody positive sample, a negative control, a concentrated washing solution containing not less than 2.5% of surfactant, Developer A containing not less than 0.3 g/L of peroxide, Developer B containing not less than 0.2 g/L of TMB, and a termination solution containing not more than 2 mol/L of sulfuric acid.

Negative control: BSA 0.5 g/L, NaCl 137 mmol/L, KCl 2.7 mmol/L, $Na_2HPO_4$ 4.3 mmol/L, $KH_2PO_4$ 1.4 mmol/L.

Concentrated washing solution: TWEEN® 20 (Polysorbate 20) 30 ml/L, NaCl 2 mol/L, KCl 54 mmol/L, $Na_2HPO_4$ 80 mmol/L, $KH_2PO_4$ 28 mmol/L.

Color developing solution A: sodium acetate 27.2 g/L, citric acid 3.2 g/L, 30% hydrogen peroxide 0.6 ml/L.

Color developing solution B: disodium EDTA 0.4 g/L, citric acid 2 g/L, glycerol 100 ml/L, 0.3 g/L TMB.

Termination solution: sulfuric acid 2 mol/L.

Preparation of 96-Well ELISA Plate Coated with 2019-nCoV-Ag:

1. The 2019-nCoV antigen fusion protein containing SEQ ID NO: 1 and protein tag (National Institute of Diagnostics and Vaccine Development in Infectious Diseases, Xiamen University) was formulated into a coating solution with 1×PBS buffer, and placed at 100 ul/well in the support plate overnight at 2-8° C.
2. PBS buffer containing 0.1% BSA was used at 200/well to perform blocking at 2-8° C. overnight.
3. The blocking solution was discarded, and drying was performed in a dry environment. Then, it was packed in an aluminum foil bag with desiccant.

Preparation of 2019-nCoV-Ag Enzyme Labeled Reagent with Horseradish Peroxidase:

1. 2019-nCoV-Ag fusion protein containing SEQ ID NO: 1 and protein tag was dialyzed into CB (pH9.6, 50 mM), in which the medium was changed more than 2 times.
2. The $ddH_2O$ solution of HRP and the $ddH_2O$ solution of $NaIO_4$ were prepared.
3. The $NaIO_4$ solution was slowly mixed with the HRP solution, and allowed to stand at 4° C. for 30 min.
4. Ethylene glycol was slowly added to the oxidized HRP solution, and allowed to stand for 30 minutes at room temperature in the dark.
5. The oxidized HRP was directly added to the fully dialyzed viral antigen protein.
6. Dialysis into CB (pH9.6, 50 mM) was continued, in which the medium was changed more than 2 times.
7. $NaBH_4$ was added to it and allowed to stand at 4° C. for 2 hours.
8. 1×PBS buffer was allowed to stand overnight, the labeling solution was added with an equal volume of 50% glycerol, mixed well and stored at −20° C.

2.2 Detection Method

1. Preparation of solution: Concentrated washing solution was diluted 20 times with distilled water or deionized water.
2. Numbering: Samples were numbered corresponding to microplates in sequence. For each plate, 3 wells of negative control, 2 wells of positive control and 1 well of blank control were set. (When dual-wavelength detection was used, blank control wells could be omitted).
3. Addition of sample: 100 µl of sample to be detected, and 50 µl of each of negative- and positive controls were added to corresponding wells, respectively.
4. Incubation: After sealing the plate with sealing film, incubation was performed at 37° C. for 30 minutes.
5. Washing plate: The sealing film was carefully removed, and the plate was washed with a plate washer 5 times, and at the end of last washing, the plate was inverted and tapped to completely drain as much as possible.
6. Addition of enzyme: 100 µl of the enzyme labeled reagent was added to each well, except for the blank well.
7. Incubation: the operation was the same as step 4.
8. Washing plate: the operation was the same as step 5.
9. Color development: 50 µl of each of color Developer A and B solutions was added to each well, gently shaken and mixed, and color development was performed at 37° C. for 15 minutes in the dark.
10. Detection: 50 µl of the termination solution was added to each well, gently shaken and mixed, and the detection results were obtained within 10 minutes. The wavelength of microplate reader was set at 450 nm (or detected with dual wavelengths of 450 nm/600-650 nm), and the A value of each well was measured after zeroing using the blank well.

Judgement of Detection Results:

1. Normal range of negative control: the A value of the negative control well was less than or equal to 0.1 (if the A value of the negative control in one well was greater than 0.1, it should be discarded; if the A values of the negative control in two or more wells were greater than 0.1, the experiment should be repeated).

2. Normal range of positive control: the A value of the positive control well was ≥0.19.

3. Calculation of cut-off value (CUTOFF): cut-off value=0.16+mean of A values of negative control wells (if the value of negative control well was lower than 0.03, it should be calculated as 0.03). Positive judgment: sample with A value≥cut-off value (CUTOFF) was positive for 2019-nCoV antibody; negative judgment: sample with A value<cut-off value (CUTOFF) was negative for 2019-nCoV antibody.

2.3 Evaluation of Detection Performance (1) The above detection kit was used as candidate reagent to detect the total antibody against 2019-nCoV in plasma samples of 49 confirmed cases from Hubei Province.

Among the 49 confirmed cases, 1 plasma sample was collected from each of 44 cases respectively, and 2 plasma samples of two different periods were collected from each of the remaining 5 cases respectively, so that a total of 54 plasma samples were collected from the confirmed cases in this experiment. The candidate reagent detected 49 positive cases, and the detection rate of the candidate reagent compared with the confirmed cases was 100.00% (49/49). For the 2 samples of two different periods for 1 case subject, the candidate reagent detected 1 negative and 1 positive, and this result was determined as a positive result of the candidate reagent.

(2) The above detection kit was as candidate reagent to detect the total antibody against 2019-nCoV in 312 serum samples of different times after onset from 81 confirmed cases of novel coronavirus infection pneumonia in Zhejiang Province and 300 serum samples from 300 other cases.

The detection results of the candidate reagent and the clinically confirmed/excluded results were analyzed by contingency table (four-fold table) for Kappa consistency test. The results showed that the sensitivity of the candidate reagent was 96.30% (95% confidence interval was 89.56% to 99.23%), the specificity was 100% (95% confidence interval was 96.38% to 100.00%), the accuracy was 99.21% (95% confidence interval was 99.72% to 99.84%), the Kappa value was 0.98, and the consistency strength was the strongest.

(3) Detection results of samples of different times after onset:

The above detection kit was used as candidate reagent to detect 2019-nCoV total antibody in plasma samples from confirmed cases of novel coronavirus pneumonia with different times after onset in Guangdong Province, and the detection results were taken together with those of samples of different times after onset in (2). The results were shown in the table below.

TABLE 3

TABLE 3-continued

Detection results of samples of different times after onset

| Days | Candidate reagent | | |
|---|---|---|---|
| after onset | Total number of detected samples (samples) | Number of positive of detection (samples) | Positive rate of detection |
| 1 | 3 | 1 | 33.33% |
| 2 | 12 | 3 | 25.00% |
| 3 | 21 | 4 | 19.05% |
| 4 | 26 | 9 | 34.62% |
| 5 | 28 | 9 | 32.14% |
| 6 | 50 | 23 | 46.00% |
| 7 | 46 | 24 | 52.17% |
| 8 | 54 | 32 | 59.26% |
| 9 | 62 | 44 | 70.97% |
| 10 | 54 | 43 | 79.63% |
| 11 | 54 | 48 | 88.89% |
| 12 | 62 | 59 | 95.16% |
| 13 | 43 | 41 | 95.35% |
| 14 | 44 | 42 | 95.45% |
| 15 | 43 | 43 | 100.00% |
| 16 | 35 | 35 | 100.00% |
| 17 | 42 | 38 | 90.48% |
| 18 | 33 | 32 | 96.97% |
| 19 | 34 | 33 | 97.06% |
| ≥20 | 96 | 94 | 97.92% |

The detection rate of the candidate reagent was 20% to 50% in the early stage of onset (before day 7), more than 90% after 12 days of onset, and almost 100% after 15 days of onset. According to different periods after onset, in the very early stage (≤3 days) and early stage (4-7 days), there were 5 and 13 patients who were negative in the nucleic acid detection, respectively, and the candidate reagent could detect 2 cases (40%) and 6 cases (46%) from them; in the middle stage (8-14 days) and late stage (≥15 days), there were 29 and 23 patients who were negative in the nucleic acid detection, and the candidate reagent could detect all of them, respectively, that was, the positive rate of detection was up to 1000%.

The above results show that the ELISA-based detection for total antibody can be used for the screening of 2019-nCoV infection, and shows a good complementary effect on the nucleic acid detection.

Example 3: Detection Kit and Method for Detecting 2019-nCoV IgM Antibody (Colloidal Gold Method)

3.1 Preparation of Detection Kit

The detection kit comprised: a glass fiber with gold-labeled novel coronavirus (2019-nCoV) antigen, a nitrocellulose membrane coated with anti-human IgM (anti-μ chain), a glass fiber, a plastic backing, a phosphate buffer-containing sample diluent, etc.

Sample diluent: NaCl 137 mmol/L, KCl 2.7 mmol/L, $Na_2HPO_4$ 4.3 mmol/L, $KH_2PO_4$ 1.4 mmol/L.

Preparation of Nitrocellulose Membrane Coated with Anti-Human IgM (Anti-μ Chain):

1. Murine anti-human IgM (p chain) (Beijing Wantai Bio-Pharmaceutical Co., Ltd.) as the material for coating test line was formulated with PBS buffer to prepare the test line coating solution; the material for coating control line was formulated with PBS buffer to prepare the control line coating solution.

2. The test line coating solution was taken and coated on the test line of the nitrocellulose membrane; the control line coating solution was taken and coated on the control line of the nitrocellulose membrane. 3. The coated nitrocellulose membrane was fully dried, packaged in an aluminum foil bag, and sealed by machine.

Preparation of glass fiber with gold-labeled novel coronavirus (2019-nCoV) antigen:

1. The 2019-nCoV antigen fusion protein containing SEQ ID NO: 1 and protein tag (National Institute of Diagnostics and Vaccine Development in Infectious Diseases, Xiamen University) as the material for gold-labeling was mixed with colloidal gold solution, added with the blocking solution to perform blocking to obtain gold-labeled solution.
2. The gold-labeled solution was added to the glass fiber, fully dried, packaged in an aluminum foil bag, and sealed by machine.

3.2 Detection Method

At room temperature, 10 μL of serum or plasma sample to be tested was added to the sample hole of test strip, then added dropwise with 2 drops of sample diluent, the test strip was horizontally placed on table, and observed to obtain results 15 minutes after adding the sample.

The judgement of the detection results was shown in FIG. 1. A: When the control line developed color and the test line also developed color, the result was judged as positive. B: When the control line developed color, while the test line did not develop color, the result was judged as negative. C: When the control line did not develop color, regardless of whether the test line developed color, the experiment was judged as invalid, and a repeated experiment was required.

3.3 Evaluation of Detection Performance (1) The above detection kit as candidate reagent was used to detect 2019-nCoV IgM antibody in plasma samples from 49 confirmed cases and 5 negative cases in Hubei Province.

Among the 49 confirmed cases, 1 plasma sample was collected from each of 44 cases respectively, 2 plasma samples of two different periods were collected from each of 2 cases respectively, and thus a total of 40 plasma samples were collected from the confirmed cases in this experiment. The candidate reagent detected 45 positive cases, and the detection rate of the candidate reagent compared with the confirmed cases was 91.84% (45/49). Among the 5 negative cases, there were 3 samples from 3 case subjects and 2 samples of two different periods from 1 case subject, with a total of 5 negative samples. The results of the five negative samples detected by the candidate reagent were all negative.

(2) The above detection kit was used as candidate reagents to detect 2019-nCoV IgM antibody in 312 serum samples and 49 whole blood samples of different times after onset from 90 confirmed cases of novel coronavirus pneumonia, and 209 serum samples and 99 whole blood samples from 308 other cases in Zhejiang Province.

The detection results of the candidate reagent and the clinically confirmed/excluded results were analyzed by contingency table (four-fold table) for Kappa consistency test. The results showed that the sensitivity of the candidate reagent was 93.33% (95% confidence interval was 86.05% to 97.51%), the specificity was 98.70% (95% confidence interval was 96.71% to 99.65%), and the accuracy was 97.49% (95% confidence interval was 95.43% to 98.79%), the Kappa value was 0.93, and the consistency strength was the strongest.

The detection results in (2) were analyzed according to different times after onset, and the results were shown in the following table.

TABLE 4

| Detection results of samples of different times after onset | | | |
|---|---|---|---|
| Days | Candidate reagent | | |
| after onset | Total number of detected samples (samples) | Number of positive of detection (samples) | Positive rate of detection |
| 1 | 1 | 0 | 0.00% |
| 2 | 4 | 0 | 0.00% |
| 3 | 4 | 0 | 0.00% |
| 4 | 9 | 2 | 22.22% |
| 5 | 7 | 0 | 0.00% |
| 6 | 12 | 0 | 0.00% |
| 7 | 18 | 4 | 22.22% |
| 8 | 12 | 2 | 16.67% |
| 9 | 18 | 6 | 33.33% |
| 10 | 22 | 9 | 40.91% |
| 11 | 25 | 19 | 76.00% |
| 12 | 22 | 13 | 59.09% |
| 13 | 20 | 16 | 80.00% |
| 14 | 21 | 18 | 85.71% |
| 15 | 20 | 18 | 90.00% |
| 16 | 15 | 12 | 80.00% |
| 17 | 19 | 15 | 78.95% |
| 18 | 19 | 18 | 94.74% |
| 19 | 16 | 14 | 87.50% |
| ≥20 | 77 | 68 | 88.31% |

It could be seen from the detection results of samples of different times after onset that with progression after onset, the detection rate of the candidate reagent increased rapidly 10 days after onset, and reached up to 80% to 90% after 13 days. The above results indicate that the IgM antibody detection based on colloidal gold method can also be used for the screening of 2019-nCoV infection.

Example 4: Detection Kit and Method for Determining 2019-nCoV Total Antibody (Colloidal Gold Method)

4.1 Preparation of Detection Kit

The detection kit comprised: a glass fiber containing gold-labeled 2019-nCoV Ag, a nitrocellulose membrane coated with 2019-nCoV Ag, a glass fiber, a plastic backing, and a phosphate buffer-containing sample diluent.

Sample diluent: NaCl 137 mmol/L, KCl 2.7 mmol/L, $Na_2HPO_4$ 4.3 mmol/L, $KH_2PO_4$ 1.4 mmol/L.

Preparation of Nitrocellulose Membrane Coated with 2019-nCoV Ag:

1. 2019-nCoV antigen fusion protein containing SEQ ID NO: 1 and protein tag as the material for coating test line was formulated with PBS buffer to prepare the test line coating solution; the material for coating control line was formulated with PBS buffer to prepare the control line coating liquid.
2. The test line coating solution was taken and coated on the test line of the nitrocellulose membrane; the control line coating solution was taken and coated on the control line of the nitrocellulose membrane.
3. The coated nitrocellulose membrane was fully dried, packaged in an aluminum foil bag, and sealed by machine.

Preparation of Glass Fiber with Gold-Labeled Novel Coronavirus (2019-nCoV) Antigen:

1. 2019-nCoV antigen fusion protein containing SEQ ID NO: 1 and protein tag (National Institute of Diagnostics and Vaccine Development in Infectious Diseases, Xiamen University) as the material for T gold-labeling was mixed with colloidal gold solution, added with the blocking solution to perform blocking to obtain gold-labeled solution.

2. The gold-labeled solution was added to the glass fiber, fully dried, packaged in an aluminum foil bag, and sealed by machine.

4.2 Detection Method

At room temperature, 10 μL of serum or plasma sample to be tested was added to the sample hole of test strip, then 2 drops of sample diluent were added dropwise, the test strip was horizontally placed on table, and observed to obtain results 15 minutes after adding the sample.

The judgement of the detection results was shown in FIG. 1. A: When the control line developed color, and the test line also developed color, the result was judged as positive. B: When the control line developed color, while the test line did not develop color, the result was judged as negative. C: When the control line did not develop color, regardless of whether the test line developed color, the experiment was judged as invalid, and a repeated experiment was required.

4.3 Evaluation of Detection Performance (1) The above detection kit was used as candidate reagent to detect the total antibody against of 2019-nCoV in plasma samples from 49 confirmed cases and 1 negative case in Hubei Province.

Among the 49 confirmed cases, 1 plasma sample was collected from each of 44 cases respectively, and 2 plasma samples of two different periods were collected from each of remaining 5 cases respectively, so that a total of 54 plasma samples from confirmed cases were collected in this experiment. The candidate reagent detected 48 positive cases, and the detection rate of the candidate reagent compared with the confirmed cases was 97.96% (48/49). For the 2 samples of two different periods from 1 case subject, the candidate reagent detected 1 negative and 1 positive, and this result was determined as a positive result of the candidate reagent. The negative sample included 1 negative sample from 1 negative case, and its detection result of the candidate reagent was negative.

(2) The above detection kit was used as candidate reagent to detect 2019-nCoV total antibody in 312 serum samples and 49 whole blood samples of different times after onset from 90 confirmed cases of novel coronavirus pneumonia, and 209 serum samples and 99 whole blood samples from 308 other cases in Zhejiang Province.

The detection results of the candidate reagent and the clinically confirmed/excluded results were analyzed by contingency table (four-fold table) for Kappa consistency test. The results showed that the sensitivity of the candidate reagent was 100.00% (95% confidence interval was 95.98% to 100.00%), the specificity was 96.75% (95% confidence interval was 94.11% to 98.43), the accuracy was 97.49% (95% confidence interval was 95.43% to 98.79%), the Kappa value was 0.93, and the consistency strength was the strongest.

The detection results in (2) were analyzed according to different times after onset, and the results were shown in the following table.

TABLE 5

Detection results of samples of different times after onset

| Days | Candidate reagent | | |
|---|---|---|---|
| after onset | Total number of detected samples (samples) | Number of positive of detection (samples) | Positive rate of detection |
| 1 | 1 | 1 | 100.00% |
| 2 | 4 | 2 | 50.00% |
| 3 | 4 | 1 | 25.00% |
| 4 | 9 | 4 | 44.44% |
| 5 | 7 | 3 | 42.86% |
| 6 | 12 | 8 | 66.67% |
| 7 | 18 | 11 | 61.11% |
| 8 | 12 | 7 | 58.33% |
| 9 | 18 | 13 | 72.22% |
| 10 | 22 | 20 | 90.91% |
| 11 | 25 | 22 | 88.00% |
| 12 | 22 | 20 | 90.91% |
| 13 | 20 | 19 | 95.00% |
| 14 | 21 | 20 | 95.24% |
| 15 | 20 | 18 | 90.00% |
| 16 | 15 | 15 | 100.00% |
| 17 | 19 | 18 | 94.74% |
| 18 | 19 | 19 | 100.00% |
| 19 | 16 | 16 | 100.00% |
| ≥20 | 77 | 76 | 98.70% |

It could be seen from the detection results of samples of different times after onset that the detection rate of the candidate reagents in the early stage of onset (before day 7) was 40% to 60%, and with progression after onset, it exceeded 90% after 10 days of onset. The above results indicate that the detection of total antibody based on the colloidal gold method can also be used for the screening of 2019-nCoV infection.

Although specific embodiments of the present invention have been described in detail, those skilled in the art will appreciate that various modifications and changes can be made to the details in light of all the teachings that have been published, and that these changes are all within the scope of the present invention. The whole of the present invention is given by the appended claims and any equivalents thereof.

What is claimed is:

1. A kit, which comprises a detection reagent and a capture reagent, wherein the detection reagent and capture reagent are each independently selected from the group consisting of (i) an isolated polypeptide and (ii) a fusion protein comprising the isolated polypeptide and an additional polypeptide;

wherein the isolated polypeptide consists of the sequence shown in SEQ ID NO: 1;

and wherein the detection reagent bears a detectable label.

2. The kit according to claim 1, which further comprises one or more reagents or devices selected from the group consisting of: (i) a device for collecting or storing a sample from a subject; (ii) an additional reagent required to perform the detection comprising buffer, diluent, blocking solution, positive control sample, and/or negative control sample.

3. A method for detecting an antibody specific to novel coronavirus (2019-nCoV) in a sample from a subject and/or for determining whether a subject has a novel coronavirus (2019-nCoV) infection, which comprises:

(1) contacting the sample with a capture reagent to obtain an immune complex;

(2) detecting the immune complex obtained in step (1) by using a detection reagent via an immunological detection to obtain a level of the antibody specific to novel coronavirus (2019-nCoV) in the sample from the subject;

and wherein the capture reagent and the detection reagent are as defined in claim 1.

4. The method according to claim 3, further comprising comparing the level with a reference value to determine whether the subject has a novel coronavirus (2019-nCoV) infection.

5. The kit according to claim 1, wherein the additional polypeptide is linked to the N-terminus or C-terminus of the isolated polypeptide directly or via a linker.

6. The kit according to claim 1, wherein the additional polypeptide is a protein tag.

7. The kit according to claim 6, wherein the additional polypeptide is selected from the group consisting of His, Flag, GST, MBP, HA, Myc, GFP and Fc.

8. The kit according to claim 1, wherein the detectable label is selected from the group consisting of enzyme, chemiluminescence reagent, fluorescent dye, colloidal gold or biotin.

9. The kit according to claim 8, wherein the enzyme is horseradish peroxidase or alkaline phosphatase.

10. The kit according to claim 8, wherein the chemiluminescence reagent is acridine ester compound.

11. The kit according to claim 1, wherein the capture reagent is attached to a surface of a solid support, or has a modifying group that can be attached to the solid support.

12. The kit according to claim 11, wherein the modifying group is biotin or avidin.

13. The kit according to claim 11, wherein the solid support is selected from the group consisting of magnetic bead, microtiter plate, and nitrocellulose membrane.

14. The kit according to claim 1, wherein the kit further comprises an instruction of using the capture reagent and the detection reagent to detect a total antibody specific to novel coronavirus (2019-nCoV) in a sample from a subject, and optionally to determine whether the subject has a novel coronavirus (2019-nCoV) infection.

15. The method according to claim 3, wherein the sample is a blood sample.

16. The method according to claim 3, wherein the sample is whole blood, plasma or serum.

17. The method according to claim 3, wherein the subject is a human.

18. The method according to claim 3, wherein the immunological detection is selected from the group consisting of enzyme immunoassay, chemiluminescence immunoassay, fluorescence immunoassay, radioimmunoassay, and immunocolloidal gold technique.

* * * * *

SEQUENCE LISTING

```
<160> NUMBER OF SEQ ID NOS: 1

<210> SEQ ID NO 1
<211> LENGTH: 223
<212> TYPE: PRT
<213> ORGANISM: Artificial sequence
<220> FEATURE:
<223> OTHER INFORMATION: 2019-nCoV S-RBD

<400> SEQUENCE: 1
```

-continued

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220
```